(12) United States Patent
Butler

(10) Patent No.: US 8,623,090 B2
(45) Date of Patent: Jan. 7, 2014

(54) SPINAL DISC PROSTHESES

(75) Inventor: Michael S. Butler, St. Charles, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 876 days.

(21) Appl. No.: 12/148,487

(22) Filed: Apr. 18, 2008

(65) Prior Publication Data

US 2008/0262622 A1 Oct. 23, 2008

Related U.S. Application Data

(60) Provisional application No. 60/925,039, filed on Apr. 18, 2007.

(51) Int. Cl.
*A61F 2/44* (2006.01)

(52) U.S. Cl.
USPC ........................................ 623/17.15

(58) Field of Classification Search
USPC ........................................ 623/17.11–17.16
See application file for complete search history.

(56) References Cited

U.S. PATENT DOCUMENTS

| | | | |
|---|---|---|---|
| 6,217,579 B1 | | 4/2001 | Koros |
| 6,447,543 B1 * | | 9/2002 | Studer et al. ............... 623/17.11 |
| 6,520,996 B1 * | | 2/2003 | Manasas et al. ............ 623/23.5 |
| 7,674,294 B2 * | | 3/2010 | Karahalios et al. ........ 623/17.11 |
| 2005/0039836 A1 | | 2/2005 | Dugan et al. |
| 2005/0055099 A1 | | 3/2005 | Ku |
| 2005/0228500 A1 * | 10/2005 | Kim et al. .................. 623/17.13 |
| 2006/0052872 A1 * | 3/2006 | Studer et al. ............... 623/17.13 |
| 2008/0021556 A1 * | 1/2008 | Edie ........................... 623/17.11 |
| 2008/0077244 A1 * | 3/2008 | Robinson ................... 623/17.16 |
| 2008/0177299 A1 * | 7/2008 | Kim et al. ..................... 606/207 |
| 2009/0118832 A9 * | 5/2009 | Ralph et al. ............... 623/17.14 |

* cited by examiner

*Primary Examiner* — Eduardo C Robert
*Assistant Examiner* — Steven Cotroneo
(74) *Attorney, Agent, or Firm* — Foley & Lardner LLP

(57) ABSTRACT

A spine disc prosthesis mimics a natural human spine disc through use of a structure that duplicates a natural Annulus Fibrosis of the disc to provide translation, extension, flexion, and axial support in like manner to a natural disc. The present spine disc prosthesis achieves this through the use of a first and second disk connected to one another via a flexible annulus fibrosis structure. The flexible annulus fibrosis structure or core is characterized by a plurality of compressible (pliant) strands that are affixed to and extend between the first and second disks. The strands are preferably, but not necessarily, situated on and extend about an outer perimeter of inside surfaces of the two end disks so as to mimic natural contours of an annulus fibrosis of a natural spinal disc. The strands may be formed by various types of biocompatible fibers, braids, cords, bundles or the like and may have a hollow core or a solid core (e.g. PEEK [polyetheretherketone] cores/core strands may also be used). The strands may be situated on the vertical, crossed or in other configurations. The end disks may be formed as to promote fusion with adjoining vertebrae when implanted. The end plate may also include a keel and/or installation structure to allow for implanting the spine disc prosthesis.

24 Claims, 11 Drawing Sheets

SPINAL DISC PROSTHESES

RELATED APPLICATIONS

This patent application claims the benefit of and/or priority to U.S. Provisional Patent Application Ser. No. 60/925,039 filed Apr. 18, 2007, entitled "Spinal Disc Prostheses" the entire contents of which is specifically incorporated herein by reference.

BACKGROUND OF THE INVENTION

1. Field of the Invention

The present invention relates to spinal disc prostheses to replace a damaged, degenerated or otherwise defective spinal disc in a spinal column of a human.

2. Background

The prior art is replete with various types of prosthetic or artificial spinal discs designed to replicate a spinal disc and thus replace a damaged, degenerated or otherwise defective spinal disc in a spinal column of a human. U.S. Pat. Nos. 5,071,437 and 5,534,030 disclose spinal disc prostheses that are typical of the prior art. The discs disclosed in these US patents include a pair of rigid plates adhered to opposite surfaces of a body of elastomeric material. Many other variations have since been developed.

The disc prosthesis when in use is positioned between adjacent vertebrae. The rigid plates may have bone in-growth material for enabling bone to adhere or fuse to the rigid plates. The disc prosthesis is subject to forces that act in the spine including compression forces due to loads on the spine, shear forces due to bending of the spine, and torsion forces due to twisting of the spine. These application forces may cause disc component failure. For example, such application forces may cause the rigid plates to separate from the body of elastomeric material in the disc prostheses of the '437 and '030 patents. Such separation would be detrimental to the proper functioning of the disc prosthesis. Moreover, these application forces have a tendency to squeeze the elastomeric body out from between the two plates. This, again, is detrimental to the proper functioning of the disc prosthesis.

When a visco-elastic material is used for the prosthetic disc body between two plates, the application forces and their attendant problems are especially true. Particularly, such spine application forces can compress a portion or more of a visco-elastic spinal disc prosthesis body from between the two plates thereof. Moreover, the application forces tend to rotate the disc body. Excess rotation can cause stress on the disc body. Such stress can lead to disc body failure in all types of prior art discs.

It is apparent from the above that prior art spinal disc prostheses fall short of providing a reliable artificial disc.

In view of the above, it is desirable to provide spinal disc prostheses that alleviate the shortcomings of the prior art.

SUMMARY OF THE INVENTION

Spine disc prostheses are presented that imitate the Annulus Fibrosis of a natural spine disc and so provide natural translation, extension, flexion and axial support within an artificial spine disc. The present spine disc prosthesis has first and second disks that are connected to one another via a flexible core. The flexible core is characterized by a plurality of compressible and/or flexible (pliant) strands extending between the upper and lower plates. The flexible core preferably, but not necessarily, extends from annular peripheries or perimeters of adjacent sides of the first and second disks in like relationship as the Annulus Fibrosis of a natural spine disc is to adjacent vertebrae of a spine. The strands may be formed as a mesh, a web, in rows, or in other configurations.

In one form, the pliant strands extend substantially perpendicular to the first and second disks. In another form, the pliant strands extend skew to the first and second disks. In this form, the pliant strands may be crisscrossed or skewed according to any number of manners or patterns. The strands are formed of a compressible and/or flexible, biocompatible material. Moreover, the strands forming the flexible core may all be of the same type or may consist of two or more types of strands as appropriate.

The pliant strands are preferably, but not necessarily, situated on and extend from the periphery of an upper side of the second disk and a lower side of the first disk. In one form, the strands are situated in a single row about the disk geometry. The disk geometry preferably mimics natural contours of a human spinal disc. The strands may be formed by various types of biocompatible fibers, braids, cords, bundles or the like and may have a hollow core or a solid core. PEEK (polyetheretherketone) cores/core strands may also be used. The strands may be situated on the vertical, crossed or in other configurations.

The end disks are preferably, but not necessarily, formed to promote fusion with adjoining vertebrae when implanted. In one form, the end disks have oval or annular frames supporting a grill or grillwork. Strands of the grillwork extend across the frame and provide openings that allow for fusion between the grillwork/frame and an adjacent vertebra when implanted. In another form, the end disks have plates shaped preferably, but not necessarily, like spine discs. Ports or openings in the end plates allow for fusion between the end plate and an adjacent vertebra when implanted. The ports, being for bone growth, may be either blind or blind with undercut. The end plate may also include a keel and/or installation structure to allow for implanting the spine disc prosthesis.

In all cases, the spinal disc prostheses may be formed in various sizes as well as be sized for lateral introduction (implantation) into a spine.

BRIEF DESCRIPTION OF THE DRAWINGS

The foregoing and other features of the present invention will become more apparent to one skilled in the art upon also reading the following description of embodiments of the invention with reference to the accompanying drawings wherein.

Figure 1:
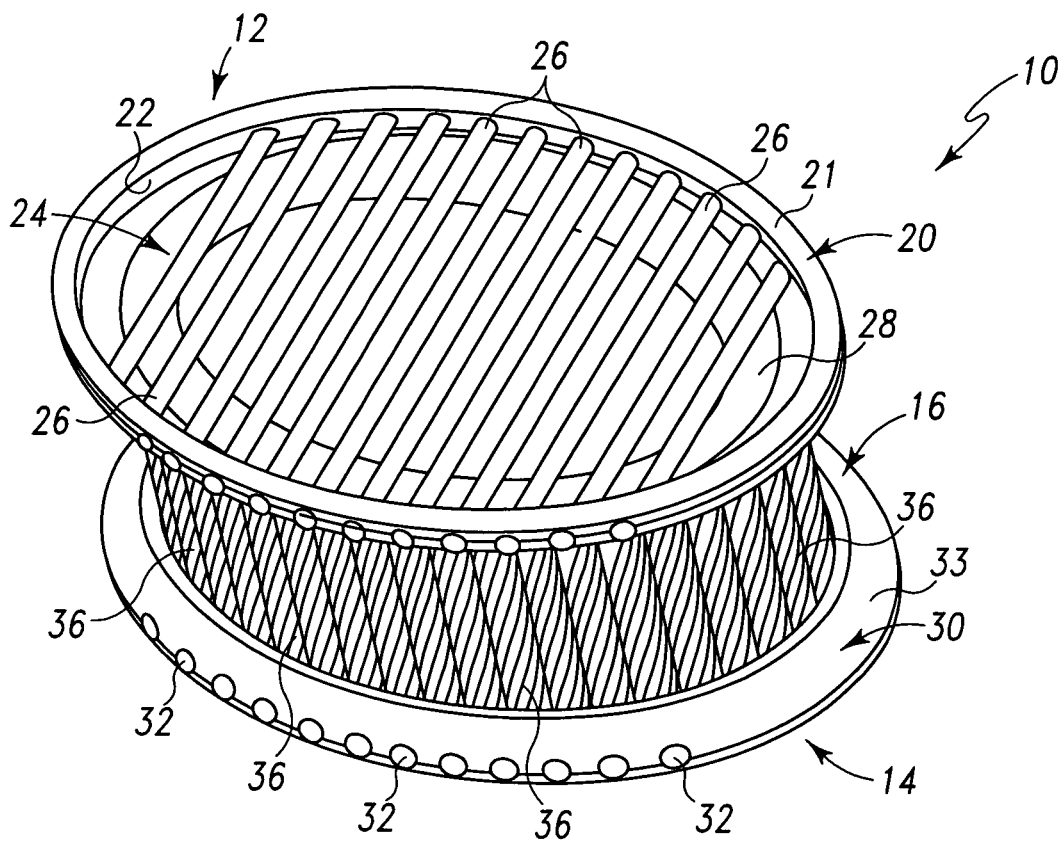
FIG. 1 is a first upper side perspective view of an embodiment of a spinal disc prosthesis fashioned in accordance with the present principles.
Figure 2:
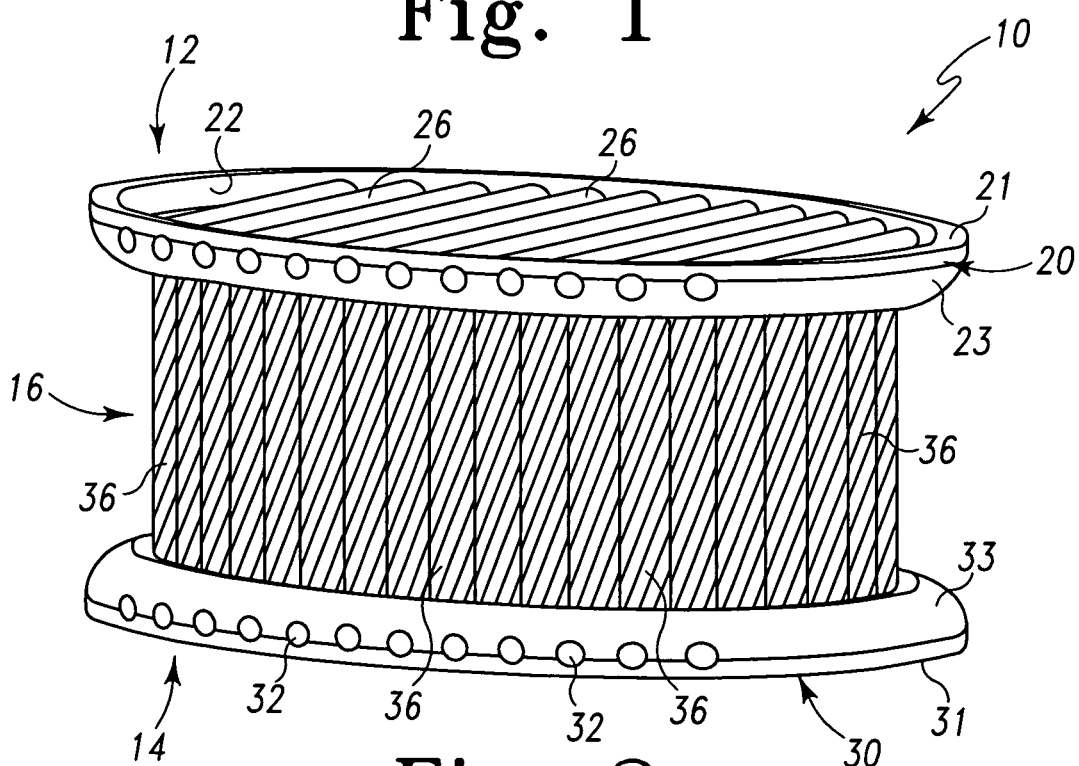
FIG. 2 is a second upper side perspective view of the spinal disc prosthesis of FIG. 1.
Figure 3:
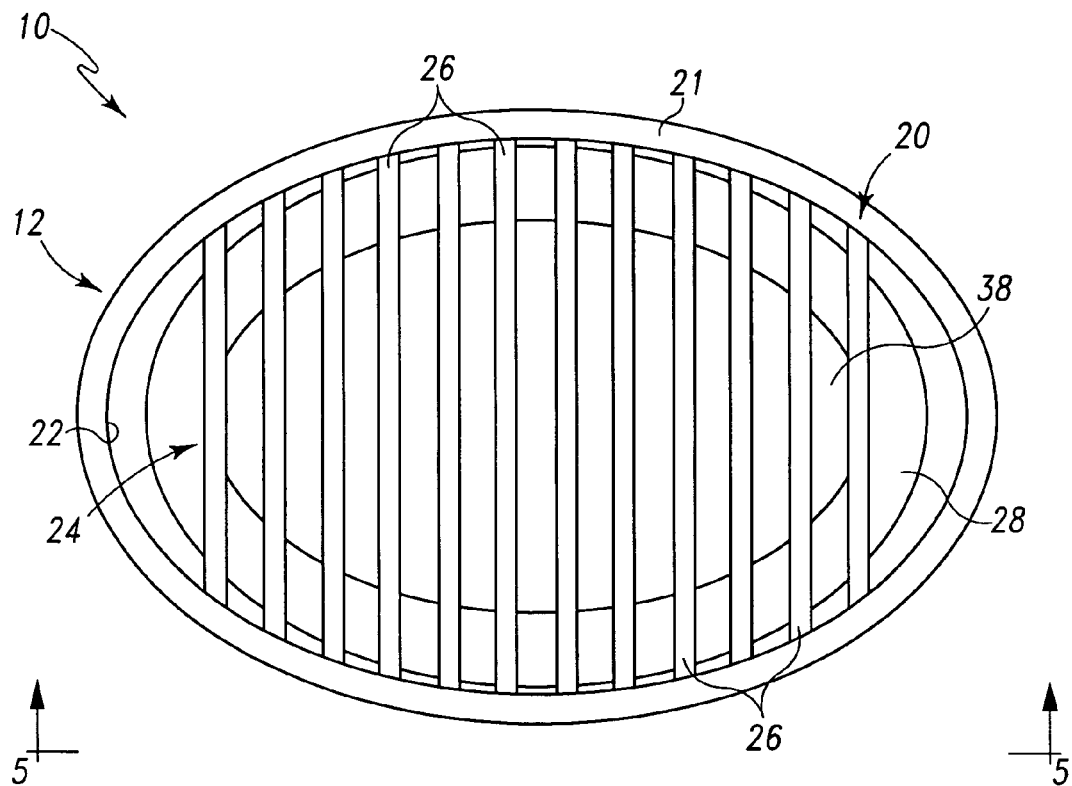
FIG. 3 is a top view of the spinal disc prosthesis of FIG. 1.
Figure 4:
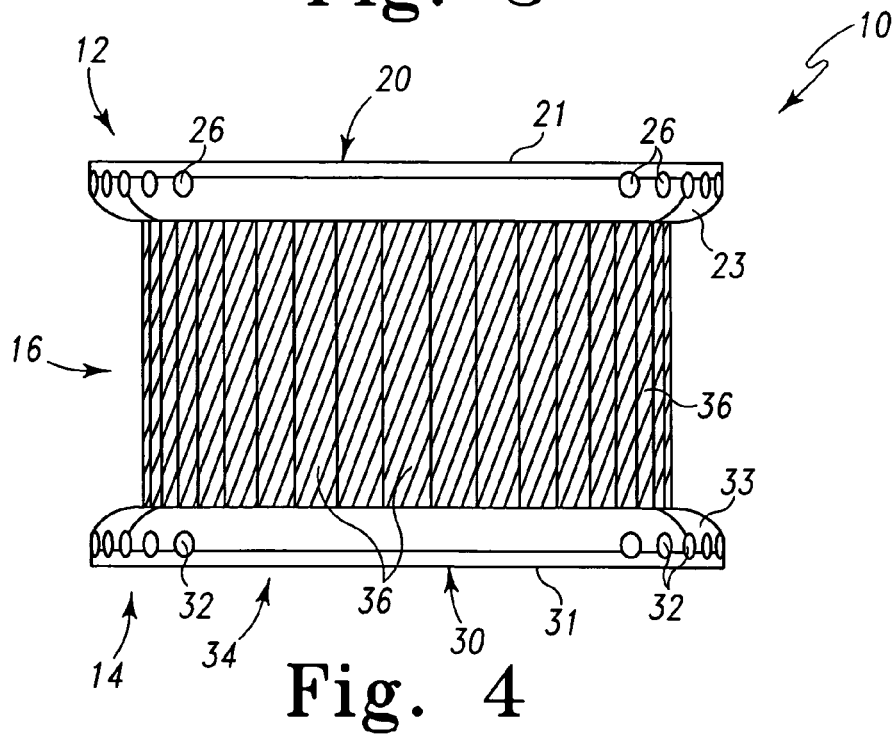
FIG. 4 is a lateral side view of the spinal disc prosthesis of FIG. 1 as taken along line 4-4 of FIG. 5.
Figure 5:
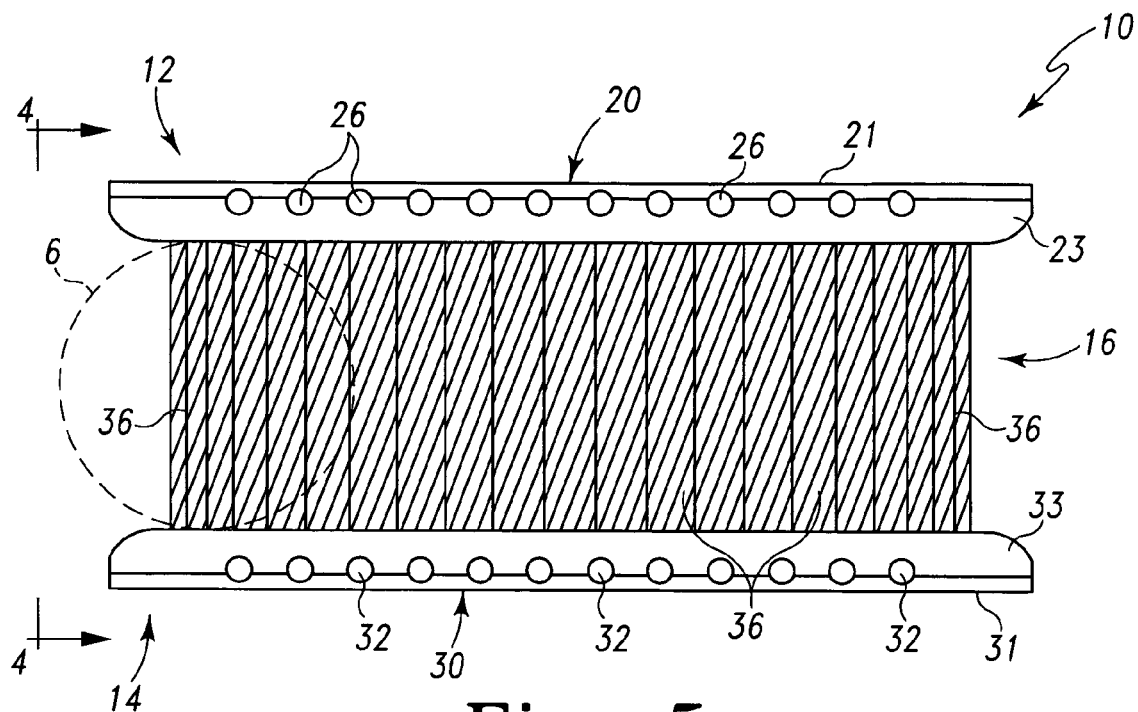
FIG. 5 is an anterior/posterior side view of the spinal disc prosthesis of FIG. 1 as taken along line 5-5 of FIG. 3.

Corresponding reference characters indicate corresponding parts throughout the several views. Although the drawings represent embodiments of the invention, the drawings are not necessarily to scale and certain features may be exaggerated in order to better illustrate and explain the present invention. The exemplifications set out herein illustrate several embodiments of the invention, but the exemplifications are not to be construed as limiting the scope of the invention in any manner.

DETAILED DESCRIPTION OF THE INVENTION

The present invention provides artificial or prosthetic spinal or spine discs (collectively, spinal disc prostheses) such as to replace damaged, degenerated, or otherwise defective or undesirable spinal discs in a spinal column of a human. FIGS. 1-6 illustrate an exemplary embodiment of a spinal disc prosthesis, i.e. spinal disc 10. The spinal disc 10 is fashioned from suitable biocompatible materials such as are known in the art. The disc 10 comprises a first end 12, a second end 14 and a middle or core 16. The nomenclature first and second is arbitrary. The first end 12 may be considered a first vertebral contacting portion while the second end 14 may be considered a second vertebral contacting portion. The core 16 may be considered an annulus fibrosis portion or hub of the spinal disc 10. The first vertebral contacting portion 12, the second vertebral contacting portion 14 and the core 16 simulates, duplicates or mimics a vertebral disc and especially the annulus fibrosis portion preferably, but not necessarily, without the nucleus pulposus (nucleus) of a disc. The first vertebral contacting portion 12 provides disc annulus fibrosis emulation and thus functions and/or provides for contact or abutment with a surface of a vertebra. The second vertebral contacting portion 14 provides disc core emulation and thus functions and/or provides for contact or abutment with a surface of an adjacent vertebra. The core 16 thus provides disc core emulation and thus functions and/or provides cushioning between the adjacent vertebrae.

The first vertebral contacting portion 12 is characterized by a preferably, but not necessarily, elliptical, oval or ovoid end, ring, frame, disk or body 20 defining an upper surface 21, an inner surface 22 and a curved lower surface 23. The elliptical body 20 supports and/or incorporates a grill, grillwork or grill structure 24 that allows for the disk top to fuse into an adjacent vertebral body (i.e. vertebra—not shown). The grill structure 24 is formed of a plurality of rods 26. The rods 26 extend between sides of the inner elliptical surface 22 of the ring 20 and therethrough (see, e.g. FIGS. 1 and 2).

The second vertebral contacting portion 14 is characterized by a preferably, but not necessarily, elliptical, oval or ovoid end, ring, frame, disk or body 30 defining a lower surface 31, an inner surface (not seen in the figures but like inner surface 22 of body 20) and a curved upper surface 33. The elliptical body 30 supports and/or incorporates a grill, grillwork or grill structure 34 (not seen in the figures but like grill structure 24 of the first end 12) that allows for the disc top to fuse into an adjacent vertebral body (i.e. vertebra—not shown). The grill structure is formed of a plurality of rods (not seen in the figures but like grill rods 26 of the grill structure 24 of the first end 12). The rods extend between sides of the inner elliptical surface of the body 30 and therethrough (see, e.g. FIGS. 1 and 2).

Figure 6:
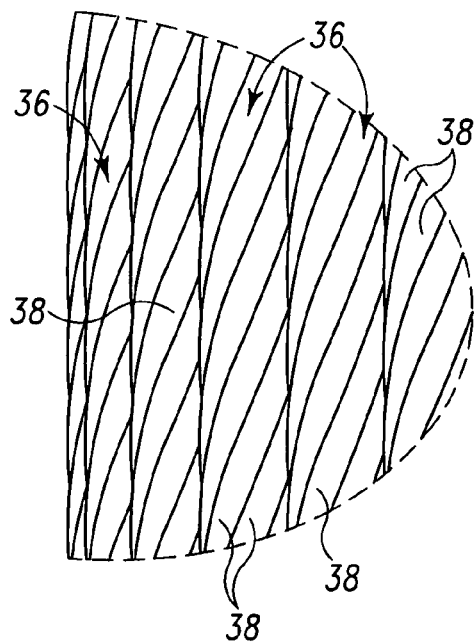
FIG. 6 is an enlarged view of a portion of the spinal disc prosthesis of FIG. 1 as taken along encircling 6-6 of FIG. 5.
Figure 7:
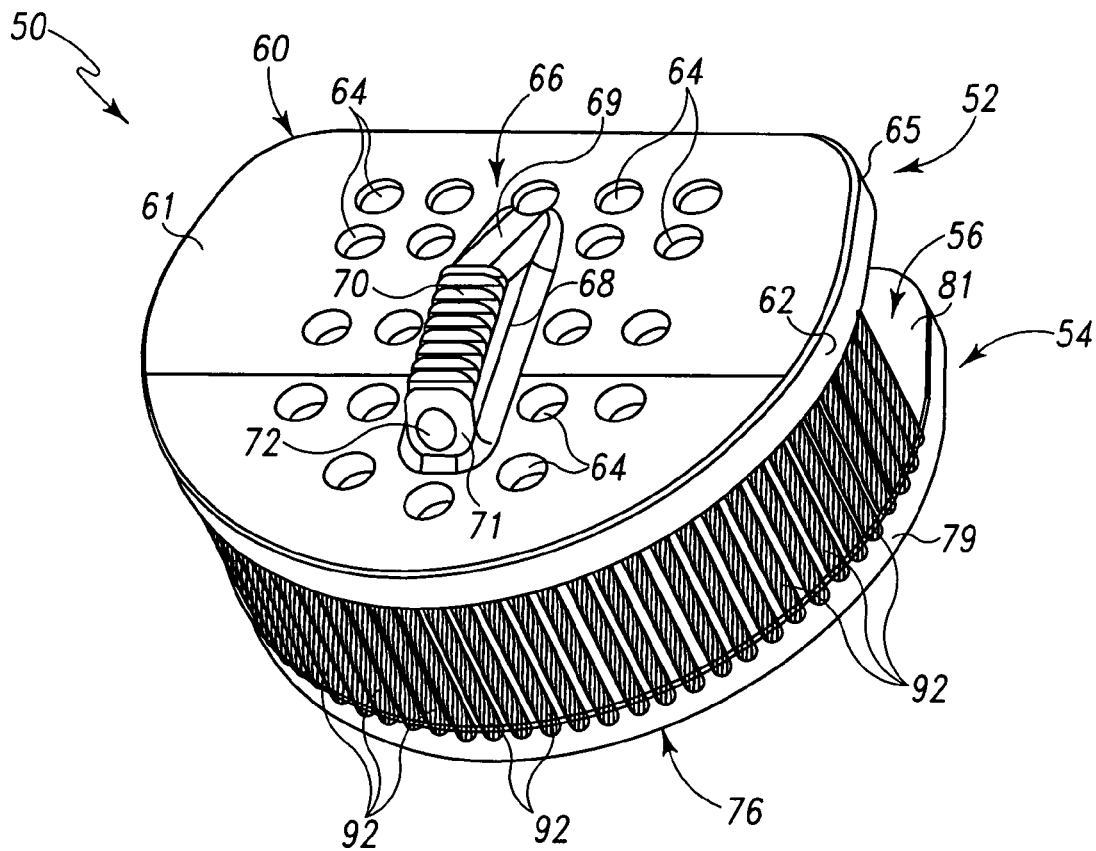
FIG. 7 is a first upper perspective view of another embodiment of a spinal disc prosthesis fashioned in accordance with the present principles.
Figure 8:
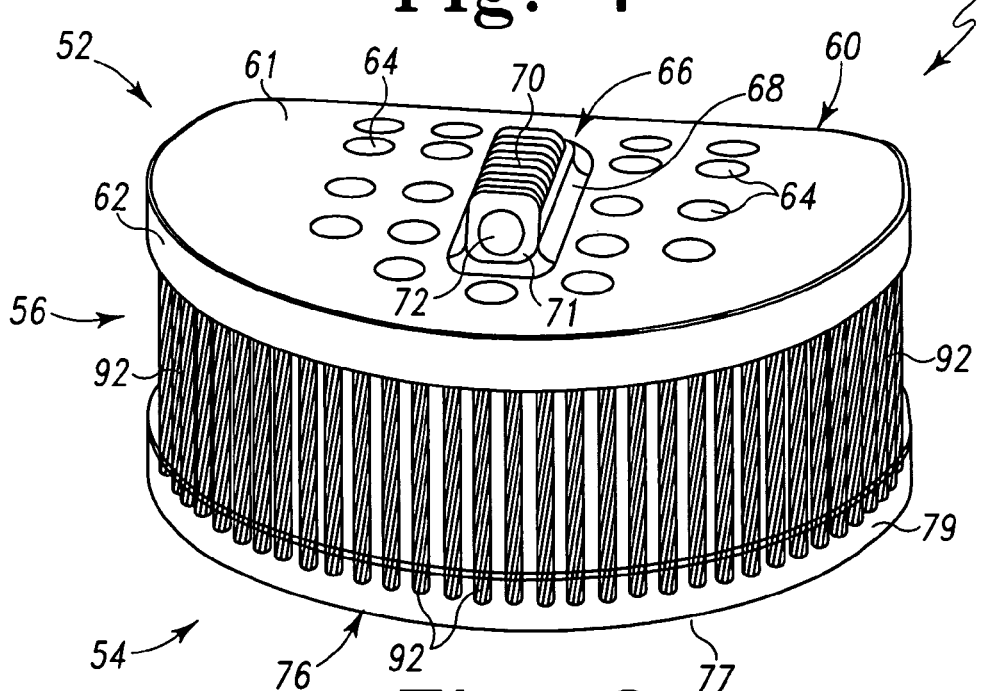
FIG. 8 is a second upper perspective view of the spinal disc prosthesis of FIG. 7.
Figure 9:
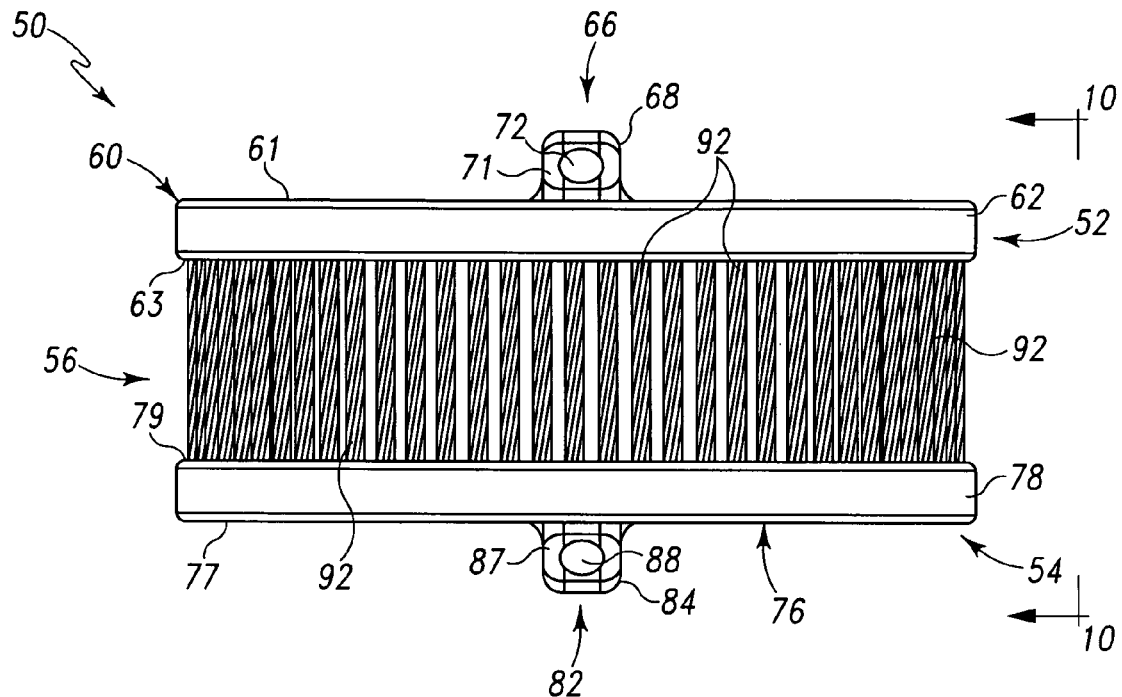
FIG. 9 is an anterior side view of the spinal disc prosthesis of FIG. 7.
Figure 10:
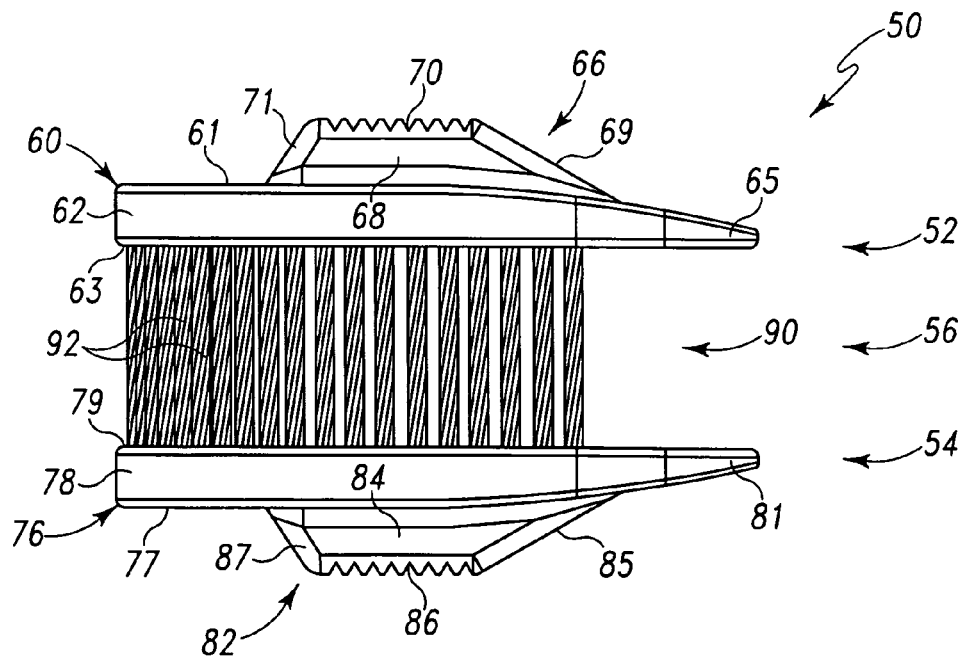
FIG. 10 is a lateral side view of the spinal disc prosthesis of FIG. 7 as taken along line 10-10 of FIG. 9.
Figure 11:
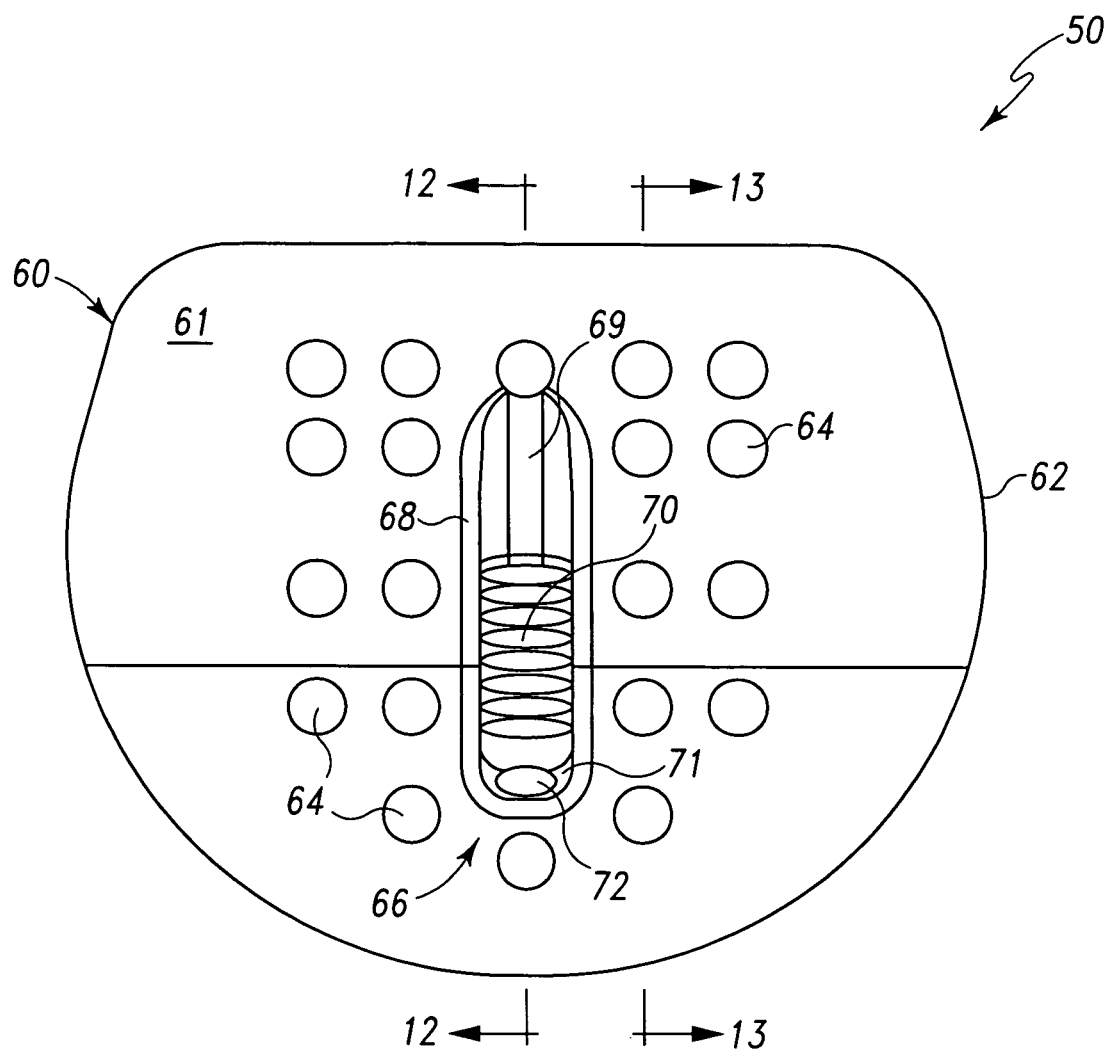
FIG. 11 is a top view of the spinal disc prosthesis of FIG. 7.
Figure 12:
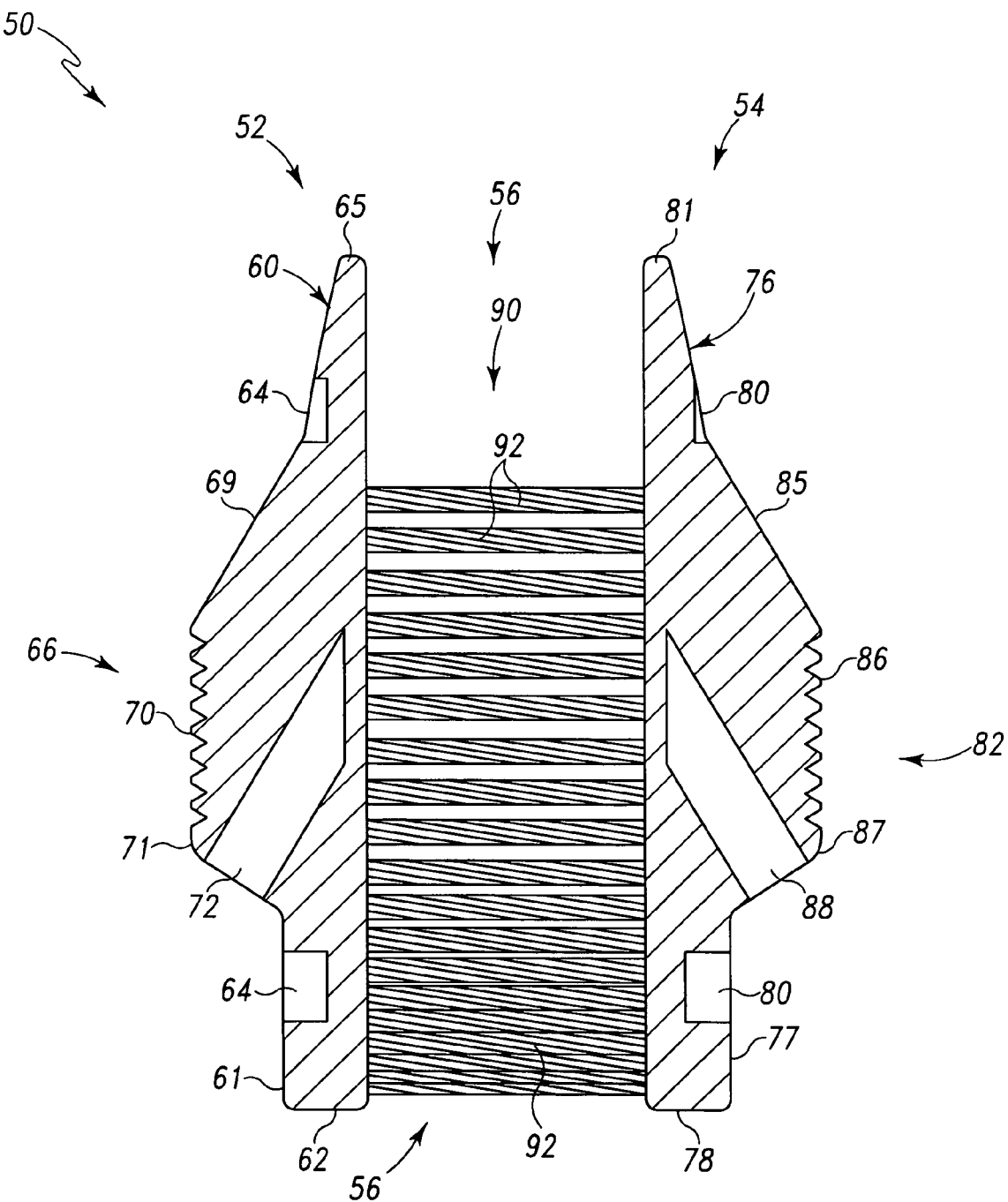
FIG. 12 is a sectional view of the spinal disc prosthesis of FIG. 7 as taken along line 12-12 of FIG. 11.
Figure 13:
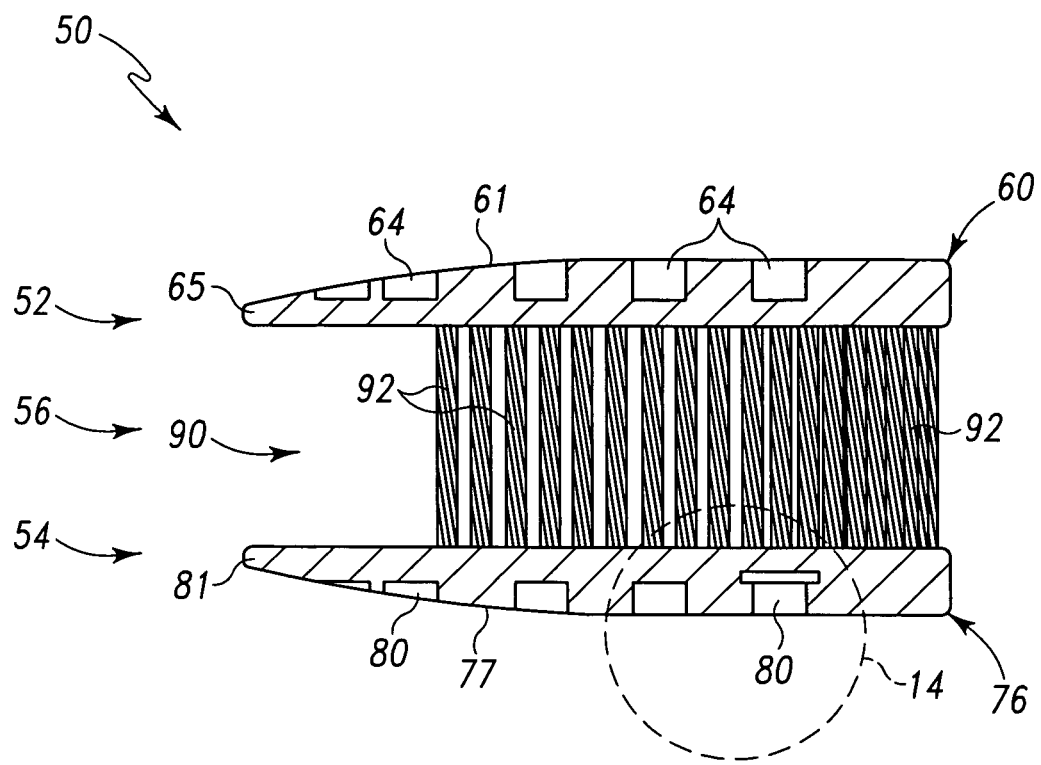
FIG. 13 is a sectional view of the spinal disc prosthesis of FIG. 7 as taken along line 13-13 of FIG. 11.

The middle, annulus fibrosis portion or core 16 has a plurality of strands, cords, braids, rope or the like (akin in one form to carpet strands) 36 that connect and extend between inner surfaces of the ends 12, 24. The end 12 or frame 20 has an elliptical opening 28. In like manner, the end 14 or frame 30 has an elliptical opening 38. The strands 36 extend about an inner periphery or diameter of the first and second rings 20, 30 of the first and second ends 12, 14. As best seen in FIG. 6, the strands 36 are preferably formed of twisted filaments, fibers or individual smaller strands 38 of the same. The number of strands and their thickness may be varied, both relative to other sizes of discs 10 or with respect to other strands of the same disc 10. The strands 36 function and/or act like a natural disc. Various exemplary strands are shown in FIGS. 17A-J encompassing strand portions 200, 300, 400, 500, 600, 700, 800, 900, 1000 and 1100.

The strands 36 are shown oriented essentially vertical, perpendicular or transverse to the ends 12, 14. It should be appreciated that the strands 36 may be oriented differently than shown. For instance, the strands 36 may be oriented in a slant or askew from one body 20 to the other body 30. Each strand may be slanted in the same direction or one or more strands may be slanted differently. Various patterns may be used. The strands may also be formed as a mesh, web or the like.

Referring now to FIGS. 7-14, there is depicted another exemplary embodiment of a spinal disc prosthesis, i.e. spinal disc 50. The spinal disc 50 is fashioned from suitable biocompatible materials such as are known in the art. The disc 50 comprises a first end 52, a second end 54 and a middle or core 56. The nomenclature first and second is arbitrary. The first end 52 may be considered a first vertebral contacting portion while the second end 54 may be considered a second vertebral contacting portion. The core 56 may be considered a annular fibrosis portion or hub of the spinal disc. The first vertebral contacting portion 52, the second vertebral contacting portion 54 and the core 56 simulates a vertebral disc and especially portions of the annulus fibrosis and nucleus pulposus (nucleus) of a disc. Particularly, the first vertebral contacting portion 52 provides disc annulus fibrosis emulation and thus functions and/or provides for contact or abutment with a surface of a vertebra. The second vertebral contacting portion 54 provides disc annulus fibrosis emulation and thus functions and/or provides for contact or abutment with a surface of an adjacent vertebra. The core 56 provides nucleus emulation and thus functions and/or provides cushioning between the adjacent vertebrae.

The first vertebral contacting portion 52 is characterized by an essentially D-shaped or spinal disc-shaped plate, body or end (or other shapes to accommodate MIS insertion) or body 60 defining an upper surface 61, a lower surface 63 and a curved peripheral or transition surface (periphery) 62. The plate 60 has a plurality of ports, holes or bores 64 formed in the upper surface 61. The ports 64 are for bone growth. A protuberance in the form of a keel or keel structure 66 extends from the upper surface 61 of the plate 60. The keel structure 66 is defined by a keel or keel body 68. The keel body 68 has a longitudinal axis about a centerline of the disc 50 (anterior-posterior axis). The posterior side has an angled or tapered surface 69 that extends from the upper surface 61 of the plate 60, in the posterior direction, and terminates at a plurality of ridges, teeth, serrations of the like 70 at the apex of the keel body 68. The front face 71 of the keel body 68 has a bore 72 that angles downwardly (see, e.g. FIG. 12). The keel 66 may take other forms, shapes or configurations but which is preferably configured as depicted in the figures.

The second vertebral contacting portion 54 is characterized by an essentially D-shaped or spinal disc-shaped (or other shapes to accommodate MIS insertion) plate, body or end 76 defining a lower surface 77, an upper surface 79 and a curved peripheral or transition surface (periphery) 78. The plate 76 has a plurality of ports, holes or bores 80 formed in the lower surface 77. The ports 80 are for bone growth. A protuberance in the form of a keel or keel structure 82 extends from the lower surface 77 of the plate 76. The keel structure 82 is defined by a keel or keel body 84. The keel body 84 has a longitudinal axis about a centerline of the disc 50 (anterior-posterior axis). The posterior side has an angled or tapered surface 85 that extends from the lower surface 77 of the plate 76, in the posterior direction, and terminates at a plurality of ridges, teeth, serrations of the like 86 at the apex of the keel body 84. The front face 87 of the keel body 84 has a bore 88 that angles downwardly (see, e.g. FIG. 12). The keel 82 may take other forms, shapes or configurations but which is preferably configured as depicted in the figures.

The middle, annulus portion or core 56 has a plurality of strands, fibers, cords, braids, rope or the like (akin to carpet strands) 92 that connect and extend between inner edges, diameters or peripheries of the plates 60 and 76. The strands 92 extend about the inner diameter of the plates 60, 76 of the first and second ends 52, 54 with the exception of area 90 (see, e.g. FIGS. 10, 12 and 13) that provides an overhang of the plates 60, 76 in which the strands 92 are inward of the periphery. In like manner to the strands 36, the strands 92 are preferably formed of twisted filaments, fibers or individual smaller strands (see, e.g. FIG. 6) of the same. The number of strands and their thickness may be varied, both relative to other sizes of discs 50 or with respect to other strands of the same disc 50. The strands 92 function and/or act like a natural disc core of a natural spine disc.

The strands 92 are shown oriented essentially vertical or perpendicular to the ends 52, 54. It should be appreciated that the strands 92 may be oriented differently than shown. For instance, the strands 92 may be oriented in a slant from one plate 60 to the other plate 76. Each strand may be slanted in the same direction or one or more strands may be slanted differently. Various patterns may be used. Meshes, webs or weaves may be fashioned via the strands. Various exemplary strands are shown in FIGS. 17A-J encompassing strand portions 200, 300, 400, 500, 600, 700, 800, 900, 1000 and 1100.

Figure 14:
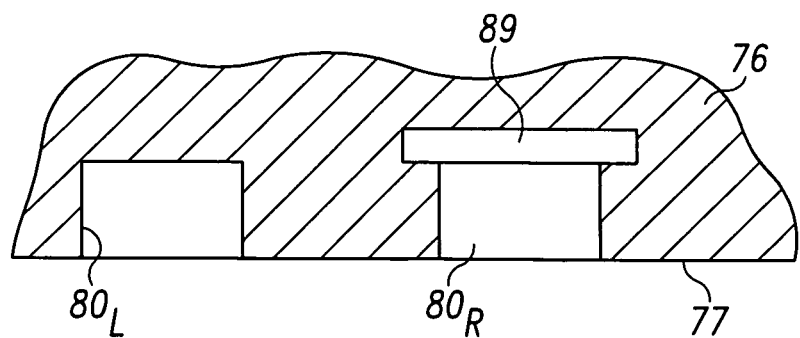
FIG. 14 is an enlarged view of a portion of the spinal disc prosthesis of FIG. 7 as taken along encircling 14-14 of FIG. 13.

FIG. 14 presents an enlarged view of a portion of the spinal disc 50 particularly illustrating ports 80 of the end 76. As the ports 80 are for bone in-growth, they may be fashioned as either blind or with an undercut. Port $80_L$ on the left side of FIG. 14 is a blind port. Port $80_R$ on the right side of FIG. 14, is a port with an undercut 89. It should be appreciated that undercuts may be provided in any, some or all of the ports 80 of the plate 76 and the ports 64 of the plate 60.

Figure 15:
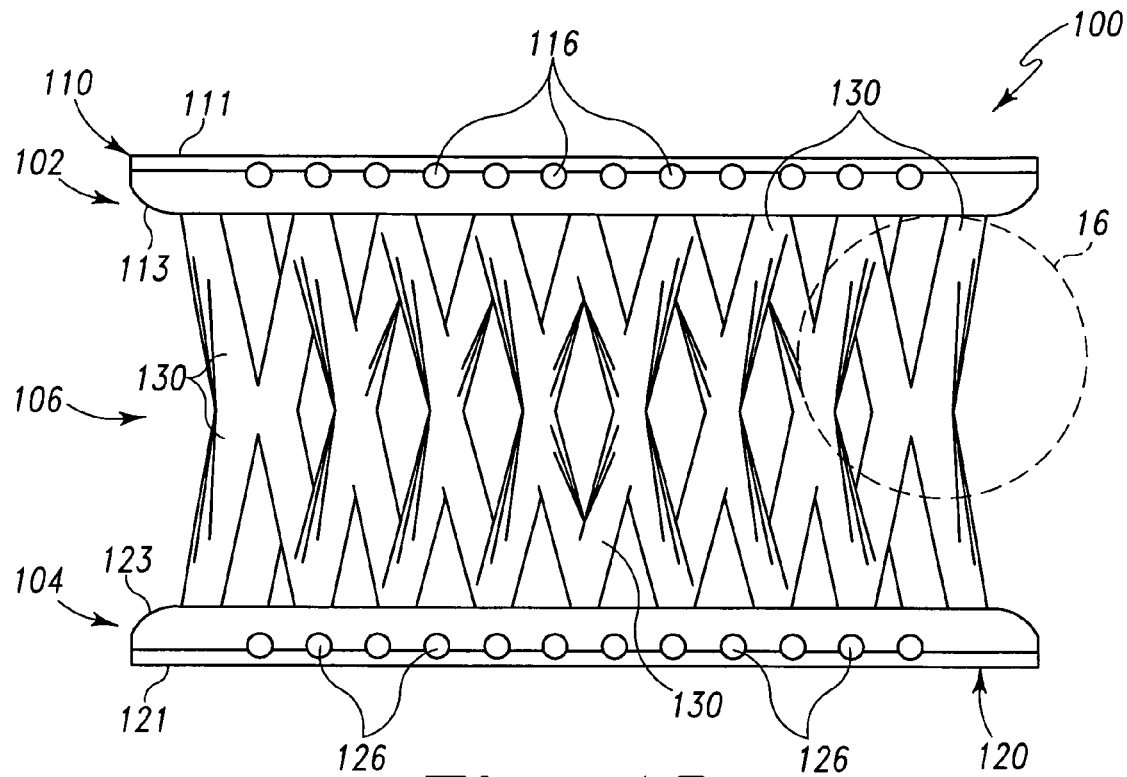
FIG. 15 is an anterior/posterior side view of another embodiment of a spinal disc prosthesis fashioned in accordance with the present principles.
Figure 16:
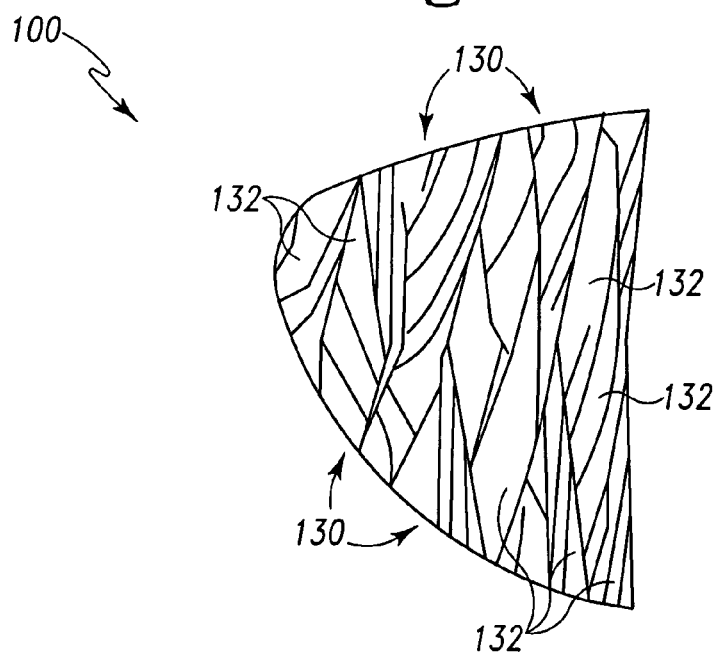
FIG. 16 is an enlarged view of a portion of the spinal disc prosthesis of FIG. 15 as taken along encircling 15-15 thereof.

FIGS. 15 and 16 depict another exemplary embodiment of a spinal disc prosthesis, i.e. spinal disc 100. The spinal disc 100 is fashioned from suitable biocompatible materials such as are known in the art. The disc 100 comprises a first end 102, a second end 104 and a middle or core 106. The nomenclature first and second is arbitrary. The first end 102 may be considered a first vertebral contacting portion while the second end 104 may be considered a second vertebral contacting portion. The middle or core 106 may be considered an annulus fibrosis portion with or without the nucleus portion. The first vertebral contacting portion 102, the second vertebral contacting portion 104 and the core 106 simulates a vertebral disc and especially portions of the annulus fibrosis of a disc. Particularly, the first vertebral contacting portion 102 provides disc annulus fibrosis emulation and thus functions and/or provides for contact or abutment with a surface of a vertebra. The second vertebral contacting portion 104 provides disc annulus fibrosis emulation and thus functions and/or provides for contact or abutment with a surface of an adjacent vertebra. The core 106 provides nucleus emulation and thus functions and/or provides cushioning between the adjacent vertebrae.

The first vertebral contacting portion 102 is characterized by a preferably, but not necessarily elliptical, oval or ovoid body, end or plate 110 defining an upper surface 111 and a curved lower surface 113. The elliptical body 110 supports and/or incorporates a grill, grillwork or grill structure (not seen but see, e.g., grill structure 24 of disc 10) that allows for the disc top to fuse into an adjacent vertebral body (i.e. vertebra). The grill structure is formed of a plurality of rods 116 the ends of which can be seen in FIG. 15. The rods 116 extend between sides of the inner elliptical surface of the body 110 and therethrough.

The second vertebral contacting portion 104 is characterized by a preferably, but not necessarily, elliptical, oval or ovoid body, end or plate 120 defining a lower surface 121 and a curved upper surface 123. The elliptical body 120 supports and/or incorporates a grill, grillwork or grill structure (not seen but see, e.g., grill structure 24 of disc 10) that allows for the disc top to fuse into an adjacent vertebral body (i.e. vertebra). The grill structure is formed of a plurality of rods 126 the ends of which can be seen in FIG. 15. The rods 126 extend between sides of the inner elliptical surface of the body 120 and therethrough.

The middle, hub, annulus fibrosis portion or core 106 has a plurality of strands or the like 130 that connect and extend between the bodies 110 and 120. The strands 106 extend about an inner periphery, perimeter or diameter of the first and second bodies 110, 120 of the first and second ends 102, 104. As best seen in FIG. 16, the strands 130 are preferably formed of twisted lines, filaments, threads or individual smaller strands 132. The number of strands and their thickness may be varied, both relative to other sizes of discs 100 or with respect to other strands of the same disc 100. The strands 130 function and/or act like a natural disc. The strands 130 are shown oriented in an X (criss-cross pattern) with respect to the ends 102, 104. Such a pattern may form a web or mesh.

Figure 17A:
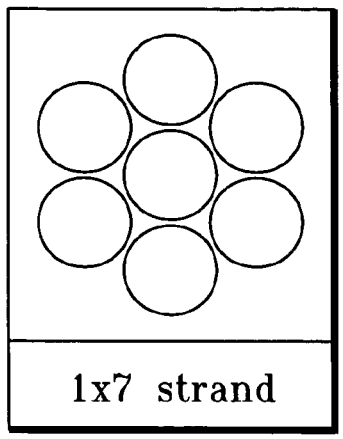
FIG. 17A is a diagrammatic cross-sectional representation of an exemplary strand as may be utilized in the spinal disc prostheses of the present invention.
Figure 17B:
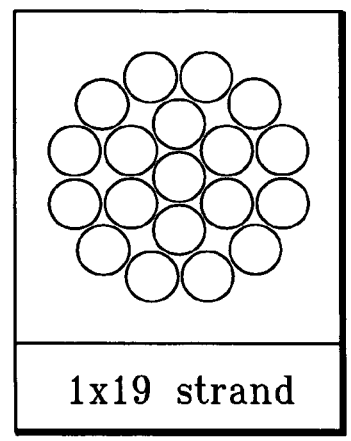
FIG. 17B is a diagrammatic cross-sectional representation of another exemplary strand for the present spinal disc/disc prostheses.
Figure 17C:
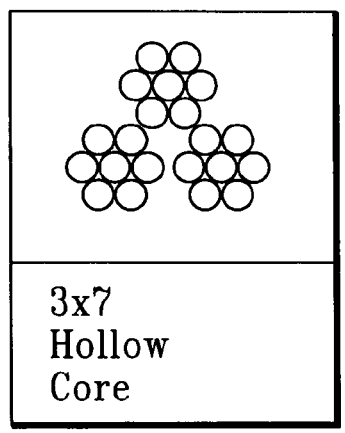
FIG. 17C is a diagrammatic cross-sectional representation of another exemplary strand as may be utilized in the spinal disc prostheses of the present invention.

FIGS. 17A-J are diagrammatic cross-sectional representations of the geometry, configuration and/or structure of various strands that may be used in the present various exemplary spinal disc/disc prostheses. FIG. 17A provides a representation of a 1×7 disc prosthesis strand 300. The strand 300 is characterized by a single middle fiber or filament and six surrounding fibers or filaments. The strand 300 is a bundled or collective braid of seven fibers so as to have or be considered as having a core. The 1×7 strand 300 may be twisted (helical) or straight. Similar to the 1×7 strand, FIG. 17B provides a representation of a 1×19 disc prosthesis strand 400 that is characterized by a single middle fiber or filament and eighteen surrounding fibers or filaments. The strand 400 is a bundled or collective braid or 20 fibers so as to have or be considered as having a core. The 1×19 strand 400 may be twisted (helical) or straight. Various 1×# combinations may be used. FIG. 17C provides a representation of a 3×7 disc prosthesis strand 500 that is characterized by three triangularly-arranged strands, each strand having seven fibers or filaments bundled or arranged or collected so as to have or be considered as having a hollow core. Variations are contemplated.

Figure 17D:
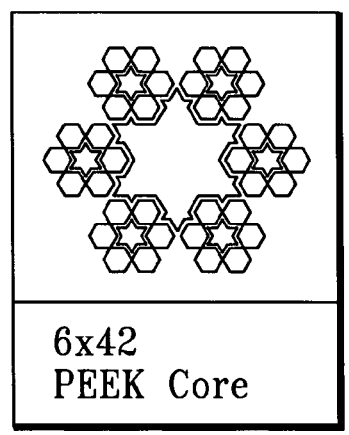
FIG. 17D is a diagrammatic cross-sectional representation of another exemplary strand as may be utilized in the spinal disc prostheses of the present invention.
Figure 17E:
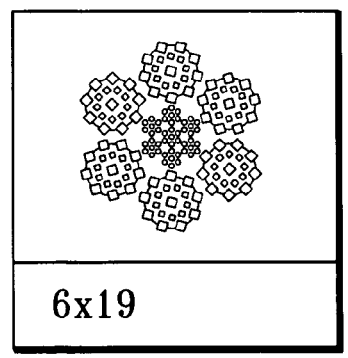
FIG. 17E is a diagrammatic cross-sectional representation of another exemplary strand as may be utilized in the spinal disc prostheses of the present invention.
Figure 17F:
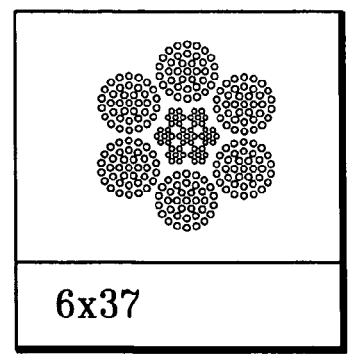
FIG. 17F is a diagrammatic cross-sectional representation of another exemplary strand as may be utilized in the spinal disc prostheses of the present invention.

The 6×42 strand 600 of FIG. 17D has a PEEK core and thus is a solid core strand. The 6×42 strand 600 is a variation of the 1×7 strand 300 (FIG. 17A) wherein a central core (1) is surrounded by six (6) strands (hence a 1×7 strand), each surrounding strand being a 1×7 strand. The cores of the surrounding 1×7 strands may or may not be PEEK. The 6×42 strand may be twisted (helical) or straight. The 6×19 strand 700 of FIG. 17E and the 6×37 strand 800 of FIG. 17F provide variations of stranded strands (and cored).

Figure 17G:
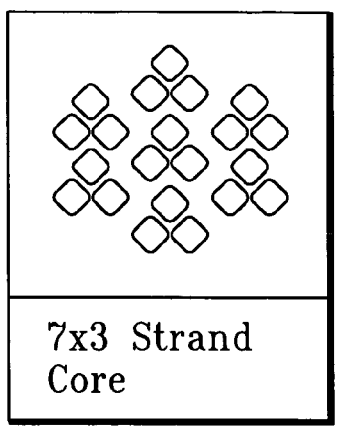
FIG. 17G is a diagrammatic cross-sectional representation of another exemplary strand as may be utilized in the spinal disc prostheses of the present invention.
Figure 17H:
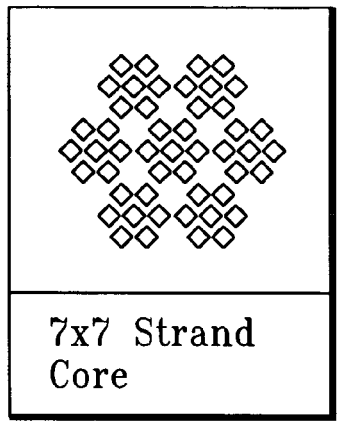
FIG. 17H is a diagrammatic cross-sectional representation of another exemplary strand as may be utilized in the spinal disc prostheses of the present invention.
Figure 17I:
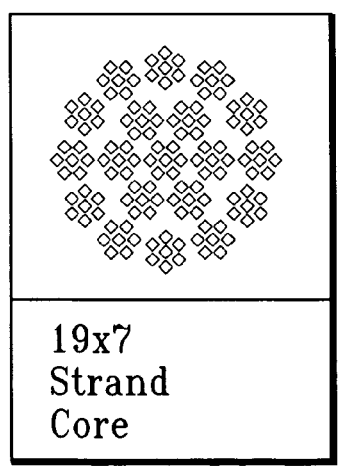
FIG. 17I is a diagrammatic cross-sectional representation of another exemplary strand as may be utilized in the spinal disc prostheses of the present invention.
Figure 17J:
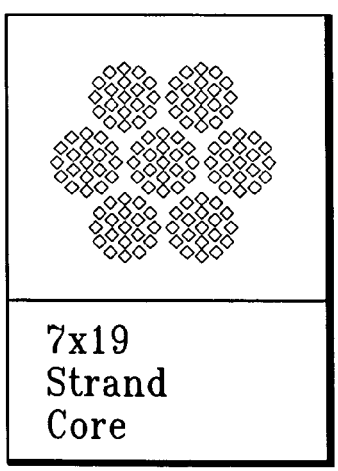
FIG. 17J is a diagrammatic cross-sectional representation of another exemplary strand as may be utilized in the spinal disc prostheses of the present invention.

FIG. 17G depicts a 7×3 strand 900 with a core as a further example of a stranded strand that is usable in the various disc prostheses presented herein. FIG. 17H depicts a 7×7 strand 100 with a core as a yet further example of a stranded strand that is usable in the various disc prostheses presented herein. A 19×7 strand 1000 and a 7×19 strand 1100 is depicted in FIGS. 17I and 17J respectively as yet further examples of stranded strands usable in the various disc prostheses presented herein.

What is claimed is:

1. A spinal disc prosthesis comprising:
a first end disk having a ring and a plurality of rods, the ring having an upper surface, a lower surface, and an inner surface defining an elliptical opening, the plurality of rods extending between and connecting sides of the inner surface of the ring;
a second end disk having a ring and a plurality of rods, the ring having an upper surface, a lower surface, and an inner surface, the plurality of rods extending between and connecting sides of the inner surface of the ring; and
a flexible core connected to and extending between the first disk and second end disk, the flexible core formed by a plurality of flexible strands extending between and coupling the ring of the first disk and the ring of the second disk;
wherein the plurality of resilient strands exclusively provide the translation, extension, flexion, and axial support for the first end disk and the second end disk.

2. The spinal disc prosthesis of claim 1, wherein the plurality of rods on the first end disk spaced-apart and substantially parallel and the plurality of rods on the second end disk are spaced-apart and substantially parallel.

3. The spinal disc prosthesis of claim 2, wherein each one of the plurality of flexible strands is formed of a single fiber.

4. The spinal disc prosthesis of claim 2, wherein each one of the plurality of flexible strands is formed of a plurality of twisted fibers.

5. The spinal disc prosthesis of claim 4, wherein each one of the plurality of flexible strands includes a core.

6. The spinal disc prosthesis of claim 5, wherein the core is comprised of PEEK.

7. The spinal disc prosthesis of claim 1, wherein:
the first end disk is defined by a first frame; and
the second end disk is defined by a second frame.

8. The spinal disc prosthesis of claim 7, wherein:
the first frame has a first open interior;
the second frame has a second open interior.

9. The spinal disc prosthesis of claim 8, wherein the first plurality of rods provide a first grillwork extending across the first open interior, and the second plurality of rods provide a second grillwork extending across the second open interior; and
wherein the flexible core extends between the lower surface of the first disk and the upper surface of the second end disk.

10. An artificial spinal disc comprising:
a first end disk having a ring and a plurality of rods, the ring having an inner surface, the plurality of rods connecting and extending between sides of the inner surface of the ring;
a second end disk having a ring and a plurality of rods, the ring having an inner surface, the plurality of rods connecting and extending between sides of the inner surface of the ring; and
a plurality of resilient strands connecting and extending between the first end disk and the second end disk and situated to form an outline of a natural annulus fibrosis of a natural spine disc within the diameter of the first and second end disks, wherein the plurality of flexible strands define an open interior between the first and second end disks, wherein the plurality of resilient strands exclusively provide the translation, extension, flexion, and axial support for the first end disk and the second end disk.

11. The artificial spinal disc of claim 10, wherein each one of the plurality of flexible strands is formed of a single fiber.

12. The artificial spinal disc of claim 10, wherein each one of the plurality of flexible strands includes a core.

13. The artificial spinal disc of claim 12, wherein the core is comprised of PEEK.

14. The artificial spinal disc of claim 10, wherein the plurality of fibers are configured as open-cored.

15. The artificial spinal disc of claim 10, wherein the plurality of flexible strands extends generally transverse to the first and second end disks.

16. The artificial spinal disc of claim 10, wherein the plurality of flexible strands extend in a generally skew manner relative to the first and second end disks.

17. The artificial spinal disc of claim 10, wherein the plurality of rods of the first end disk extend through the ring of the first end disk.

18. The artificial spinal disc of claim 10, wherein:
the ring of the first end disk has a first open interior;
the ring of the second end disk has a second open interior.

19. The artificial spinal disc of claim 18, wherein:
the ring of the first disk is a continuous annular structure; and
the ring of the second disk is a continuous annular structure.

20. A prosthetic spinal disc comprising:
a first ovoid ring supporting a first grill structure formed by a plurality of spaced-apart, substantially parallel rods connecting and extending through opposing sides of inner surfaces of the first ovoid ring;
a second ovoid ring supporting a second grill structure formed by a plurality of spaced-apart, substantially parallel rods connecting and extending through opposing sides of inner surfaces of the second ovoid ring; and
a flexible mesh extending between and connecting the first and second ovoid ends and contoured in a line duplicating a natural Annulus Fibrosis of a natural human spinal disc, the flexible mesh including a plurality of separate adjacent resilient strands connecting and extending between a lower surface of the first ovoid ring and an upper surface of the second ovoid ring, wherein the plurality of resilient strands exclusively provide the translation, extension, flexion, and axial support for the first and second ovoid rings.

21. The prosthetic spinal disc of claim 20, wherein the flexible mesh is formed of a plurality of flexible strands.

22. The prosthetic spinal disc of claim 21, wherein the plurality of flexible strands are formed of a plurality of twisted fibers.

23. The prosthetic spinal disc of claim 20, wherein the plurality of flexible strands extend substantially perpendicular between the first ovoid ring and the second ovoid ring.

24. The artificial spinal disc of claim 23, wherein:
the first ovoid ring has a first open interior;
the second ovoid ring has a second open interior; and
the artificial spinal disc further comprises a second grill structure extending across the second open interior.

* * * * *